(12) United States Patent
Beck

(10) Patent No.: US 8,030,314 B2
(45) Date of Patent: Oct. 4, 2011

(54) USE OF 2H-BENZIMIDAZOL-2-ONE, 1,3-DIHYDRO-1-(2{4-[3-(TRIFLUOROMETHYL)PHENYL]-1-PIPERAZINYL}ETHYL)- AND ITS PHYSIOLOGICALLY ACCEPTABLE ACID ADDITION SALTS

(76) Inventor: Jürgen K. Beck, Munster (DE)

( * ) Notice: Subject to any disclaimer, the term of this patent is extended or adjusted under 35 U.S.C. 154(b) by 1408 days.

(21) Appl. No.: 10/473,525

(22) PCT Filed: May 10, 2002

(86) PCT No.: PCT/EP02/05182
§ 371 (c)(1),
(2), (4) Date: May 4, 2004

(87) PCT Pub. No.: WO02/092088
PCT Pub. Date: Nov. 21, 2002

(65) Prior Publication Data
US 2004/0180904 A1    Sep. 16, 2004

(30) Foreign Application Priority Data

May 11, 2001   (EP) ................................. 01111195

(51) Int. Cl.
*A61K 31/497*    (2006.01)
*C07D 211/32*    (2006.01)
(52) U.S. Cl. .................... 514/254.06; 546/199
(58) Field of Classification Search .............. 514/254.06; 546/199
See application file for complete search history.

(56) References Cited

U.S. PATENT DOCUMENTS 5,925,627 A    7/1999    Baker et al.

FOREIGN PATENT DOCUMENTS

| | | |
|---|---|---|
| FR | 2 768 338 | 3/1999 |
| WO | WO 98/42344 | 10/1998 |

OTHER PUBLICATIONS

Rang, H.P., Dale, M.M., Ritter, J.M., and P. Gardner, (1995). Pharmacology. Churchill Livingstone, New York. pp. 527-529.*
Nakazato et al. Brain Research, 2002, vol. 930, pp. 134-142.*
Trends in Neurosciences. Oct. 2000, vol. 23, Supplement 1, pp. S71-S77.*
Evans, S.E. Gilbert, et al; "The effects of flibanserin on amphetamine withdrawal-induced hypolocomotion in rats", Society for Neuroscience Abstracts, (1998), vol. 24, No. 1-2, pp. 2133.
Borsini F., et al.: Behavioral effects of flibanserin (BIMT 17), Pharmacology, Biochemistry and Behavior (Sep. 1999) 64 137-46.
Gupta, Y.K., et al.; "Therapeutic Potentials of 5-HT Receptor Modulators" Indian Journal of Pharmacology; vol. 26, No. 2,; (Jun. 1, 1994), pp. 94-107.
Borsini, F., et al.; "BIMT 17, a $5\text{-HT}_{2A}$ receptor antagonist and $5\text{-HT}_{1a}$ receptor full agonist in rat cerebral cortex"; Naunyn-Schmiedebergs Archives of Pharmacology, (Sep. 1995), 352 (3); pp. 276-282.
Podhorna, J. et al.; "Flibanserin has anxiolytic effects without locomotor side effects in the infant rat ultrasonic vocalization model of anxiety"; British Journal of Pharmacology, (Jun. 2000) 130 (4) pp. 739-746.

* cited by examiner

*Primary Examiner* — Shengjun Wang
*Assistant Examiner* — Samira Jean-Louis
(74) *Attorney, Agent, or Firm* — Connolly Bove Lodge & Hutz LLP

(57) ABSTRACT

Use of 2H-benzimidazol-2-one, 1,3-dihydro-1-(2{4-[-(trifluoromethyl)phenyl]-1-piperazinyl}ethyl)- or a physiologically acceptable acid addition salt thereof, for the manufacture of a medicament for the treatment of extrapyramidal movement disorders. These extrapyramidal movement disorders may result from idopathic Parkinson's disease, from the adverse effects of the administration of anti-Parkinson drugs in idiopathic Parkinson's disease, from dyskinesias caused by idiopathic Parkinson's disease and/or long-term administration of anti-Parkinson drugs, from Parkinson-like or Parkinson-related syndromes of from Parkinsonoid symptoms. Another aspect of the present invention concerns a pharmaceutical composition comprising, as active ingredients-(I) 2H-benzimidazol-2-one, 1,3-dihydro-1-(2-{4-[3-(trifluoromethyl)phenyl]-1-piperazinyl}ethyl)-or a physiologically acceptable acid addition salt thereof, and (II) at least one anti-Parkinson drug, in combination with one or more pharmaceutically acceptable excipients.

5 Claims, No Drawings

USE OF 2H-BENZIMIDAZOL-2-ONE, 1,3-DIHYDRO-1-(2{4-[3-(TRIFLUOROME-THYL)PHENYL]-1-PIPERAZINYL}ETHYL)- AND ITS PHYSIOLOGICALLY ACCEPTABLE ACID ADDITION SALTS

The present invention is related to the use of 2H-benzimidazol-2-one, 1,3-dihydro-1-(2-{4-[3-(trifluoromethyl)phenyl]-1-piperazinyl}ethyl)- or a physiologically acceptable acid addition salt thereof, for the manufacture of a medicament for the treatment of extrapyramidal movement disorders.

The compound 2H-benzimidazol-2-one, 1,3-dihydro-1-(2-{4-[3-(trifluoromethyl)phenyl]-1-piperazinyl}ethyl)- is a known substance having a structure according to the following general formula (I)

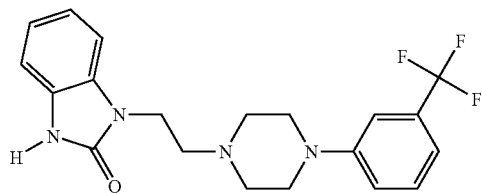

(I)

and is commonly known under the International Non-Proprietary Name "flibanserin". In the following, this term "flibanserin" is used in order to describe the compound 2H-benzimidazol-2-one, 1,3-dihydro-1-(2-{4-[3-(trifluoromethyl)phenyl]-1-piperazinyl}ethyl)-.

Flibanserin is said to show activities as a $5-HT_{1A}$ agonist and $5-HT_{2A}$ antagonist and is therefore under investigation for its central serotonergic activity and usefulness in the treatment of central nervous system (CNS) disorders. Typical CNS disorders include affective disorders (for example depression and bipolar disorders), anxiety, sleep and sexual disorders, psychosis, schizophrenia, personality disorders, mental organic disorders and mental disorders in childhood, aggressiveness, age associated memory impairment, cerebral ictus and motion sickness. The term "motion sickness" is typically used to describe vestibular related disturbances, for example such as travel sickness or kinetosis and physical acceleration related difficulties.

Due to expected central serotonergic activity, flibanserin is currently under development by Boehringer Ingelheim as an antidepressant (company communications, dated May 1996 and March 1997). According to pharmaceutical data base information "flibanserin activated the 5-HT inhibitory response and reduced forskolin-stimulated cAMP accumulation ($EC_{50}$=913 nM) and antagonized 5-HT-induced PI turnover (Ki=113 nM) in the rat cortex. It dose-dependently inhibited rat cortical firing rate. These data indicate that it is the first direct postsynaptic compound which activates the 5-HT inhibitory response at the cortical level (19th CINP (Washington, D.C.), 1994, Abs 0-24-10). It has potential in anxiety disorders and psychoses (Company pipeline, February 1998)."

The inventor as named to the present application has made investigations, experiments and other research work with flibanserin and related 2H-benzimnidazol-2-one, 1,3-dihydro-1-(2-{4-[3-(trifluoromethyl)phenyl]-1-piperazinyl}ethyl)-derivates and has found novel and useful activities of flibanserin promising new pharmaceutical applications beyond of the known treatment of CNS disorders.

Starting therefrom, it is the technical problem (objective) of the present invention to provide novel pharmaceutical uses of 2H-benzimidazol-2-one, 1,3-dihydro-1-(2-{4-[3-(trifluoromethyl)phenyl]-1-piperazinyl}ethyl)-, termed flibanserin and its physiologically acceptable acid addition salts.

Accordingly, a first aspect of the present invention is related to the use of flibanserin or a physiologically acceptable acid addition salt thereof for the manufacture of a medicament for the treatment of extrapyramidal movement disorders.

A second aspect of the present invention is related to the use of flibanserin or a physiologically acceptable acid addition salt thereof in combination with at least one conventional anti-Parkinson drug for the manufacture of a pharmaceutical combination preparation for the treatment of extrapyramidal movement disorders caused by idiopathic Parkinson's disease or by related Parkinson syndromes or by choreatic syndromes, or by symptoms such as several types of tremor,and/or for relief of the adverse effects of the administration of anti-Parkinson drugs, neuroleptic drugs, anti-depressants and/or antiemetics/prokinetik drugs.

A third aspect of the present invention is related to a pharmaceutical composition comprising, as active ingredients 2H-benzimidazol-2-one, 1,3-dihydro-1-(2-{4-[3-(trifluoromethyl)phenyl]-1-piperazinyl}ethyl)-, or a physiologically acceptable acid addition salt thereof, and at least one anti-Parkinsonian drug, in combination with one or more pharmaceutically acceptable excipients.

Preferably, the 2H-benzimidazol-2-one, 1,3-dihydro-1-(2-{4-[3-(trifluoromethyl)phenyl]-1piperazinyl}ethyl)- compound (flibanserin) is in the form of its physiologically acceptable acid addition salt as formed with hydrochloric acid, sulfuric acid, maleic acid or fumaric acid.

In the following, the present invention is described in more detail.

The underlying results of investigations and research work confirm a therapeutic activity of flibanserin against extrapyramidal movement disorders. The extrapyramidal motoric system (EPS) denotes a specific region out of the central nervous system that is involved in the steering of movements. The target structures of flibanserin that are the $5-HT_{1A}$ and $5-HT_{2A}$ receptors are located in that brain region. Typical disorders of the EPS include idiopathic Parkinson's disease, adverse effects of the administration of conventional anti-Parkinson drugs and neuroleptic drugs, and antiemetics/prokinetic drugs and toxins, further Parkinson-like and Parkinson-related syndromes such as dyskinetic syndromes, dystonic syndromes (including tic diseases, blepharospasm, Meige syndrome, spastic torticollis, and the like), further choreatic syndromes, the several types of tremor, Gilles de la Tourette syndrome, ballism, myoclonus, restless legs syndrome or Wilson's disease and other kinds of extrapyramidal motoric disturbances. The known applications of flibanserin are related to psychiatric diseases and complaints. Contrary thereto, the present invention refers to the use of flibanserin in neurological indications.

Therefore, the present invention provides a novel use of flibanserin or physiologically acid addition salts thereof for the manufacture of a medicament intended for the treatment of extrapyramidal movement disorders. Further the present invention provides a novel use of flibanserin or physiologically acid addition salts thereof for the manufacture of a medicament intended for the treatment of extrapyramidal movement disorders such as caused by idiopathic Parkinson's disease, adverse effects of the administration of conventional anti-Parkinson drugs and neuroleptic drugs, antiemetics/prokinetic drugs and toxins, further caused by Parkinson-like and Parkinson-related syndromes such as dyskinetic syndromes, dystonic syndromes (including tic diseases, blepharospasm, Meige syndrome, spastic torticollis, and the like), further choreatic syndromes, the several types of tremor, further Gilles de la Tourette syndrome, ballism, myoclonus, restless legs syndrome or Wilson's disease and other kinds of extrapyramidal motoric disturbances.

Especially, flibanserin shows activity against extrapyramidal movement disorders caused by treatments of idiopathic Parkinson's disease. Therefore, the present invention provides the use of 2H-benzimidazol-2-one, 1,3-dihydro-1-(2-{4-[3-(trifluoromethyl)phenyl]-1-piperazinyl}ethyl)- or a physiologically acceptable acid addition salt thereof, for the manufacture of a medicament for the treatment of extrapyramidal movement disorders resulting from idiopathic Parkinson's disease.

Typical anti-Parkinson drugs include l-dopa (levodopa), amantadine, biperiden, metixen, budipine, metoclopramid, selegiline and the like, further dopamine agonists such as apomorphine, bromocriptine, α-dihydro-ergocriptine, cabergoline, lisuride, pramipexol, ropinirol and pergolide. Levodopa is degraded by dopa decarboxylase. A number of known anti-Parkinson drugs contain levodopa along with dopa decarboxylase blocking agents such as carbidopa and benserazid. The administration of levodopa and of said dopa decarboxylase blocking agents provides a sufficient amelioration of the motor disturbances in early stages of Parkinson's disease. However, long-term application over several years induces adverse effects. Typical adverse effects of said kind include several types of dyskinesias such as choreic, dystonic, ballistic and myoclonic dyskinesia, as well as motoric fluctuations. Often, the limiting factor of an anti-Parkinson treatment with levodopa and/or dopamine agonists is based on those dyskinesias. Flibanserin meliorates the adverse effects of these anti-Parkinson drugs and of these dopa decarboxylase blocking agents.

In order to investigate the efficacy of flibanserin in the treatment of levodopa-induced dyskinesias, experiments in a primate model of Parkinson's disease were performed. 6 common marmosets (callithrix jacchus) that developed chronical Parkinsonian motor deficits after MPTP administration were treated orally with levodopa plus carbidopa for 3 weeks according to the procedure described by Pearce et al. (1995). After several days the animals started to demonstrate signs of dyskinesias. The severity of dyskinesias was measured by assessing the extent of choreic and dystonic movements in all parts of the body. An administration of flibanserin in addition to levodopa significantly reduced said dyskinesias. In some of the monkeys with less severe dyskinesia those symptoms disappeared entirely. Surprisingly, the effect of levodopa on rigidity and bradykinesia was not weakened.

This, in general favorable activity of flibanserin for the treatment of extrapyramidal movement disorders and this specific, dyskinesia reducing effect of flibanserin common with standard anti-Parkinson drugs in long term treated Parkinson patients is a new and additional effect, differently and far beyond an antipsychotic effect to be expected for flibanserin due to its $5\text{-}HT_{2A}$ antagonistic activity.

A pharmacological CNS action such as antipsychotic has been found and described for a number of neuroleptic, $5\,HT_{2A}$ antagonistic drugs, for example such as clozapine (Meltzer 1994). An antipsychotic (CNS) efficacy in Parkinson's disease has already been proven (Meltzer et al., 1995). In analogy, the same antipsychotic (CNS) effect may be expected under treatment with flibanserin in addition to its favorable anti-dyskinetic properties.

Moreover, the preclinical profile of flibanserin provides evidence that said compound may be additionally used as an antidepressant and axiolytic (Rueter L. E. et al. 1998, Synapse 29; 392-405). These and other expected CNS activities of flibanserin provide additional pharmalogical activities in addition and beyond the extrapyramidal movement disorders meliorating activity of flibanserin according to the present invention.

The reason of developing Parkinson's disease is a chronic process leading to a loss of dopaminergic neurons in a certain area of the EPS (substantia nigra). That process may be simulated in an experiment using cultured dopaminergic cells (from fetal rat mesencephalic tissue) which are exposed to a selective toxin (6-hydroxydompamine). The experiments were conducted in accordance with the method of Michel and Hefti, 1990. When the toxin was added to the cell culture medium the survival time of the neurons was markedly diminished. However, when the toxin was co-administered along with flibanserin the survival time increased in a concentration-dependent manner and reached normal survival times at concentrations of 0.1 to 1 μM flibanserin. This indicates additionally neuroprotective properties of flibanserin. On the basis of these experiments it can be expected that patients treated with flibanserin will take benefit from said neuroprotective effect by slowing down or stopping the progression of the disease. Moreover, if flibanserin is given in early stages of the disease, a steady process leading to more severe stages may be postponed or even avoided. In particular, the occurrence of levodopa-induced dyskinesias can be prevented. In-so-far, a synergistic effect of the common administration of conventional anti-Parkinson drugs along with flibanserin in the treatment of Parkinson's disease is to be expected as increased "ON"-periods and decreased "OFF"-periods may be obtained.

Therefore, flibanserin possesses a favourable therapeutic effect in the treatment of levodopa-induced dysinesias in Parkinson patients that was not recognized so far. The mechanism of action is based on a synergistic interaction with two different types of serotonergic receptors. Propably, this mechnism enables in addition beneficial effects for the patients by reducing also the other most frequent complications of long-term treatment with anti-parkinson drugs such as for example hallucinosis, depression and anxiety.

Therefore, the present invention provides the use of 2H-benzimidazol-2-one, 1,3-dihydro-1-(2-{4-[3-(trifluoromethyl)phenyl]-1-piperazinyl}ethyl)- or a physiologically acceptable acid addition salt thereof, for the manufacture of a medicament for the treatment of extrapyramidal movement disorders attributed to the administration and metabolism of conventional anti-Parkinson drugs, for example such as levodopa, amantadine, biperiden, metixen, budipine, metoclopramid, selegiline and the like, and further of dopamine agonists such as for example apomorphine, bromocriptine, dihydro-ergocriptine, cabergoline, lisuride, ropinirol and pergolide, and/or of the conventional dopa decarboxylase blocking agents such as carbidopa and benserazid.

The clinical appearance of levodopa-induced dyskinesias and of tardive dyskinesias are very often similar. Tardive dyskinesias are frequently observed in chronic schizophrenic patients after long-term treatment with neuroleptics. Recently an animal model of tardive dyskinesia was developed by Eyles at al. 2000. Persistent tardive dyskinesias were induced in 6 baboons by application of a derivative of haloperidol for 41 weeks until the animals developed abnormal orofacial signs that were consistent with tardive dyskinesia. These symptoms persisted during the drug-free period. The extent of dyskinesias was assessed by using a score derived fromt that applied in humans (Abnormal Involuntary Movement Scale). There was a significant improvement of dyskinesias by more than 50% after application of flibanserin. That means that flibanserin is also helpful in the treatment of tardive dyskinesia in chronic schizophrenic patients.

Therefore, the present invention provides the use of 2H-benzimidazol-2-one, 1,3-dihydro-1-(2-{4-[3-(trifluoromethyl)phenyl]-1-piperazinyl}ethyl)- or a physiologically acceptable acid addition salt thereof, for the manufacture of a medicament for the treatment of extrapyramidal movement disorders resulting from tardive dyskinesia in chronic schizophrenic patients.

As well known in the art, the administration and metabolism of certain neuroleptic drugs acting via a blocking of the D2 receptors for example such as haloperidol, risperidone, olanzapine, amisulpride, sulpiride, chlorpromazin, promazin, levopro sucazin, perphenazin, pluphenazin, thioridazin and/or certain antiemetics/prokinetic drugs administered against the troubles of motion sickness, for example such as metoclopramid may generate similar kinds of extrapyramidal movement disorders commonly termed Parkinsonoid symptoms. Flibanserin shows activity against said Parkinsonoid like extrapyramidal movement disorders attributed to the administration of said neuroleptic drugs and antiemetics/prokinetic drugs.

Therefore, the present invention provides the use of 2H-benzimidazol-2-one, 1,3-dihydro-1-(2-{4-[3-(trifluoromethyl)phenyl]-1-piperazinyl}ethyl)- or a physiologically acceptable acid addition salt thereof, for the manufacture of a medicament for the treatment of extrapyramidal movement disorders, especially Parkinsonoid-like extrapyramidal movement disorders, as attributed to the administration of said neuroleptic drugs and antiemetics/prokinetic drugs.

Further, there is a number of Parkinson-like or Parkinson-related syndromes, for example such as dyskinetic syndromes, dystonic syndromes, priming of motor disturbances and other kinds of motoric fluctuations, multi-systems atrophy, progressive supranuclear palsy, corticobasalic degeneration, olivio-ponto cerebellar atrophy and/or Shy-Drager-syndrome, causing similar extrapyramidal movement disorders. Flibanserin shows activity against said Parkinson-like or Parkinson-related syndromes such as dyskinetic syndromes, dystonic syndromes, priming of motor disturbances and other kinds of motoric fluctuations, multi-systems atrophy, progressive supranuclear palsy, corticobasalic degeneration, olivio-ponto cerebellar atrophy and/or Shy-Drager-syndrome.

Therefore, the present invention provides the use of 2H-benzimidazol-2-one, 1,3-dihydro-1-(2-{4-[3-(trifluoromethyl)phenyl]-1-piperazinyl}ethyl)- or a physiologically acceptable acid addition salt thereof, for the manufacture of a medicament for the treatment of extrapyramidal movement disorders caused by or attributed with Parkinson like or Parkinson related syndromes such as dyskinetic syndromes, dystonic syndromes, priming of motor disturbances and other kinds of motoric fluctuations, multi-systems atrophy, progressive supranuclear palsy, corticobasalic degeneration, olivio-ponto cerebellar atrophy and/or Shy-Drager-syndrome.

Further, flibanserin will be helpful to meliorate the adverse effects of anti-Parkinson drugs and similar drugs administered to treat the fore-mentioned Parkinson-like or Parkinson-related syndromes.

Therefore, the present invention provides the use of 2H-benzimidazol-2-one, 1,3-dihydro-1-(2-{4-[3-(trifluoromethyl)phenyl]-1-piperazinyl}ethyl)- or a physiologically acceptable acid addition salt thereof, for the manufacture of a medicament for the treatment of extrapyramidal movement disorders arising as adverse effects of the administration of anti-Parkinson drugs and similar drugs in the treatment of Parkinson-like or Parkinson-related syndromes such as dyskinetic syndromes, dystonic syndromes, priming of motor disturbances and other kinds of motoric fluctuations, multi-systems atrophy, progressive supranuclear palsy, corticobasalic degeneration, olivio-ponto cerebellar atrophy and/or Shy-Drager-syndrome.

According to another unexpected finding, flibanserin shows activity against extrapyramidal movement disorders accompanied with chorea and choreatic syndromes such as Huntington's disease, chorea minor and pregnancy related chorea.

Therefore, the present invention provides the use of 2H-benzimidazol-2-one, 1,3-dihydro-1-(2-{4-[3-(trifluoromethyl)phenyl]-1-piperazinyl}ethyl)- or a physiologically acceptable acid addition salt thereof, for the manufacture of a medicament for the treatment of extrapyramidal movement disorders accompanied with chorea and choreatic syndromes such as Huntington's disease, chorea minor and pregnancy related chorea.

According to another unexpected finding flibanserin shows remarkable effects in the treatment of extrapyramidal movement disorders provoking symptoms such as several types of tremor and/or symptoms related to Gilles de la Tourette syndrome, restless legs syndrome, ballism, myoclonus and Wilson's disease.

Therefore, the present invention provides the use of 2H-benzimidazol-2-one, 1,3-dihydro-1-(2-{4-[3-(trifluoromethyl)phenyl]-1-piperazinyl}ethyl)- or a physiologically acceptable acid addition salt thereof, for the manufacture of a medicament for the treatment of extrapyramidal movement disorders provoking symptoms such as several types of tremor, and/or symptoms related to Gilles de la Tourette syndrome, restless legs syndrome, ballism, myoclonus and Wilson's disease.

As stated above, there is a number of conventional anti-Parkinson drugs containing active ingredients such as for example levodopa, amantadine, biperiden, metixen, budipine, metoclopramid, selegiline and the like, further dopamine agonists such as for example apomorphine, bromocriptine, α-dihydro-ergocriptine, cabergoline, lisuride, pramipexol, ropinirol and pergolide. Further, it is known to provide said anti-Parkinson drugs in the form of a combination preparation containing in addition to said active anti-Parkinson principle at least ane aditional compound, for example decarboxylase inhibitors such as benserazid or carbidopa. As already stated above, flibanserin meliorates the adverse effects caused by an administration of these anti-Parkinson drugs and/or of these dopa decarboxylase blocking agents.

Therefore, a second and preferred aspect of the present invention is related to a pharmaceutical composition comprising, as active ingredients
  (I) 2H-benzimidazol-2-one, 1,3-dihydro-1-(2-{4-[3-(trifluoromethyl)phenyl]-1-piperazinyl}ethyl)- or a physiologically acceptable acid addition salt thereof, and
  (II) at least one anti-Parkinson drug,
    in combination with one or more pharmaceutically acceptable excipients.

Preferably, the present invention provides a pharmaceutical combination preparation comprising flibanserin in a fixed pharmaceutical composition with a conventional anti-Parkinson drug having a potential to elicit dyskinetic side effects or having an impact on dyskinesias already present and caused by a long-term administration of said anti-Parkinson drug.

The additional content of flibanserin in said pharmaceutical combination preparation enables:
- either to improve the efficacy of the other drug on Parkinson's symptoms without significant dyskinetic side effects, and/or
- to reduce the dyskinetic side effects at a dosage of the other drug needed to control Parkinson's symptoms.

According to a preferred embodiment, said pharmaceutical composition may comprise as active ingredients
- (I) 2H-benzimidazol-2-one, 1,3-dihydro-1-(2-{4-[3-(trifluoromethyl)phenyl]-1-piperazinyl}ethyl)- or a physiologically acceptable acid addition salt thereof, and
- (II) at least one conventional anti-Parkinson drug or conventional dopamin agonists, and
- (III) a conventional dopamine decarboxylase blocking agent, in combination with one or more pharmaceutically acceptable excipients.

Preferably, said conventional anti-Parkinson principle is a drug selected from a group including levodopa, amantadine, biperiden, metixen, budipine, metoclopramid, selegiline, and other substances having anti-Parkinson activity.

Preferably, said conventional dopamine agonist is a drug selected from a group including apomorphine, bromocriptine, α-dihydro-ergocriptine, cabergoline, lisuride, pergolide, pramipexol, ropinirol, and other known dopamine agonists.

Preferably, said conventional dopa decarboxylase blocking agent is benserazid or carbidopa.

Preferably, flibanserin, that is 2H-benzimidazol-2-one, 1,3-dihydro-1-(2-{4-[3-(trifluoromethyl)phenyl]-1-piperazinyl}ethyl)- is in the form of its physiologically acceptable acid addition salt formed with hydrochloric acid, sulfuric acid, maleic acid or fumaric acid.

As stated above the compound 2H-benzimidazol-2-one, 1,3-dihydro-1-(2-{4-[3-(trifluoromethyl)phenyl]-1-piperazinyl}ethyl)- having a structure according to the following general formula (I)

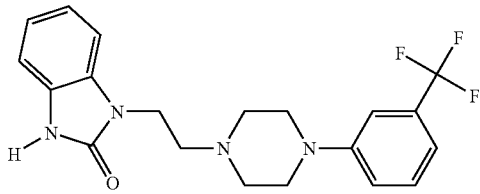

(I)

and termed in this application documents in short "flibanserin" due to its registered INN is a known substance. Suited methods of manufacture and purifaction in order to obtain the substance in a purity suited for pharmaceutical application are well known in the art.

The substance according to the general formula (I) and prepared according to these known methods may optionally be converted by inorganic or organic acids into non-toxic, physiologically acceptable acid addition salts, for example by conventional methods such as by reacting the substance as a free base with a solution of the corresponding acid in a suitable solvent. Examples of non-toxic physiologically acceptable acid addition salts are those formed with hydrochloric, nitric, sulfuric, phosphoric, maleic, fumaric, citric, tartaric, acetic, benzoic, succinic, gluconic, lactic, glycinic, malic, mucoic, glutamic, isethionic, ascorbic, or sulphamic adic. Particularly preferred acids are hydrochloric acid, sulfuric acid, maleic acid and fumaric acid.

As already stated above, a preferred embodiment of the present invention is related to a pharmaceutical composition having the form of a combination preparation and comprising as active ingredients each an active amount of
- (I) the substance according to the general fomula (I) or a physiologically acceptable acid addition salt thereof
- (II) a conventional anti-Parkinson drug, and optionally an active amount of
- (III) a conventional dopa decarboxylase blocking agent in association with one or more pharmaceutical carriers, diluents or excipients. For pharmaceutical administration said ingredients may be incorporated into the conventional pharmaceutical preparations in solid, liquid or spray form. The compositions may, for example, be presented in a form suitable for oral, rectal, parenteral administration or for nasal inhalation. Preferred forms include, for example, capsules, tablets, coated tablets, ampoules, suppositories and nasal spray.

The active ingredients may be incorporated in excipients or carriers conventionally used in pharmaceutical compositions such as, for example, talc, arabic gum, lactose, gelatine, magnesium stearate, corn starch, aqueous or non-aqueous vehicles, polyvinylpyrrolidone, semisynthetic glycerides of fatty acids, sodium phosphate, EDTA, polysorbate 80. In order to increase the solubility of the compounds of general formula (I) or their physiological acceptable salts, surfactants, non-ionic surfactants such as PEG 400, cyclodextrins, metastable polymorphs, inert absorbents such as bentonite may be incorporated.

The composition are advantageously formulated in dosage units, such that each dosage unit being adapted to supply a single dose of flibanserin. Typically, each dosage unit may conveniently contain from 0,01 mg to 100 mg and preferably from 0,1 mg to 50 mg flibanserin even more preferred between approximately 1 and 20 mg flibanserin. The composition may be administered once or more times a day for example 2, 3, or 4 times daily. The specific dose for each patient depends on all sorts of factors, for example on the age, body weight, general state of health, on sex, diet, time and route of administration, on the excretion rate, pharmaceutical substance combination and on the severity of the particular disorder to which the therapy relates. Oral administration is preffered, but also parenteral routes of administration (for example intravenous or transdermal or nasal) may be used.

The following examples refer to typical pharmaceutical compositions according to the present invention and should by no means be construed as defining the scope of the invention.

EXAMPLE 1

Tablets Containing Flibanserin

The following components

| | |
|---|---|
| flibanserin hydrochloride | 15 parts by weight |
| lactose | 182 parts by weight |
| corn starch | 50 parts by weight |
| magnesium stearate | 3 parts by weight | are provided. At first, flibanserin, lactose and corn starch were mixed and homogeneously moistened with water. After screening of the moist mass-and drying in a tray drier, the mixture was again passed through a screen and magnesium stearate was added. Then the mixture was pressed into tablets weighing 250 mg each. Each tablet contains 15 mg of flibanserin hydrochloride.

EXAMPLE 2

Tablets Containing Flibanserin, Levodopa and Benserazide

The following components

| flibanserin hydrochloride | 1 parts by weight |
| levodopa | 50 parts by weight |
| benserazide | 10 parts by weight |
| lactose | 200 parts by weight |
| talc | 10 parts by weight |
| magnesium stearate | 5 parts by weight | are tableted in a custamory manner to obtain tablets each comprising 0,2 mg flibanserin hydrochloride, 10 mg levodopa and 2 mg benserazide.

EXAMPLE 3

Capsules

A homogenous mixture is prepared from the following ingredients

| flibanserin hydrochloride | 15 parts by weight |
| lactose | 183 parts by weight |
| magnesium stearate | 2 parts by weight | and filled into hard gelatine capsules such that each capsule contains 200 mg of said mixture.

EXAMPLE 4

Suppositories

Providing the following components

| flibanserin hydrochloride | 1 parts by weight |
| semisynthetic glycerides of fatty acids | 49 parts by weight | and melting the semisynthetic glycerides of fatty acids to obtain a hmogenous melt. Thereafter, introducing the powder flibanserin hydrochloride into said melt while stirring homogenously. Following cooling, the fattty mass-is pressed into preformed mouldes for suppositiories. Each suppository comprises a weight of 1.200 mg and contains 24 mg flibanserin hydrochloride.

Related Scientific Literature

Bonifati-V; Fabrizio-E; Cipriani-R; Vanacore-N; Meco-G
Buspirone in levodopa-induced diykinesias.
Clin-Neuropharmacol. 1994 February; 17(1); 73-82
Eyles-D W; Pond-S M, Van-der Schyf-C J; Haliay-G M
Mitochondrial ultrastructure and density in a primate model of persistant tardive dyskinesia Life-Sci. 2000 February 25; 66(14); 1345-50
Goa-K L; Ward-A
Buspirone. A repliminary review of its pharmacological properties and therapeutic efficacy as an anxiolytic.
Drugs. 1986 August; 32(2); 112-29
Meltzer-H Y
An overview of the mechanism of action of clozapine.
J-Clin-Psychiatry. 1994 September; 55 Suppl B; 47-52
Meltzer-H Y; Kennedy-J; Dai-J; Parsa-M; Riley-D
Plasma clozapine levels and the treatment of L-DOPA-induced psychosis in Parkinson's disease. A high potency effect of clozapine.
Neurophysopharmacology. 1995 February; 12(1); 39-45
Michel-P P; Hefti-F
Toxicity of 6-hydroxydopamine and dopamine for dopaminergic neurons in culture.
J-Neurosci-Res. 1990 August; 26(4); 428-35
Pearce-R K; Jackson-M; Smith-L; Jenner-P; Marsden-C D
Chronic L-DOPA administration induces dyskinesias in the 1-methyl-4-phenyl-1,2,3,6-tetrahydropyridine-treated common marmoset (Callithrix Jacchus).
Mov-Disord. 1995 November; 10(6); 731-40
Shoulson-I
DATATOP; a decade of neuroprotective inquiry. Parkinson Study Group.
Deprenyl And Tocopherol Antioxidative Therapy Of Parkinsonism.
Ann-Neurol. 1998 September; 44(3 Suppl 1); S160-6
Semkowa-I; Wolz-P; Krieglstein-J
Neuroprotective effect of 5-HT$_{1A}$ receptor agonist, Bay X 3702, demonstrated in vitro and in vivo.
Eur-J-Pharmacol. 1998 Oct. 23; 359(2-3); 251-60

The invention claimed is:

1. A method for the treatment of extrapyramidal movement disorders in the form of levodopa-induced dyskinesias which comprises administering to an idiopathic Parkinson's disease patient in need thereof an amount effective for treating extrapyramidal movement disorders in the form of levodopa-induced dyskinesias of 2H-Benzimidazol-2-one, 1,3-dihydro-1-(2-{4-[3-(trifluoromethyl) phenyl]-1-] [piperazinyl}ethyl) (flibanserin) or a physiologically acceptable acid addition salt thereof.

2. The method according to claim 1, wherein said 2H-Benzimidazol-2-one, 1,3-dihydro-1-(2-{4-[3-(trifluoromethyl) phenyl]-1-][piperazinyl}ethyl) (flibanserin) is in the form of its physiologically acceptable acid addition salt formed with hydrochloric acid, sulfuric acid, maleic acid or fumaric acid.

3. The method according to claim 1 wherein the 2H-benzimidazol-2-one, 1,3-dihydro-1-(2-{4-[3-(trifluoromethyl) phenyl]-1-][piperazinyl}ethyl) (flibanserin) is employed in a dosage amount of 0.01 mg to 100 mg.

4. The method according to claim 1 wherein the 2H-benzimidazol-2-one, 1,3-dihydro-1-(2-{4-[3-(trifluoromethyl) phenyl]-1-][piperazinyl }ethyl) (flibanserin) is employed in a dosage amount of 0.1 mg to 50 mg.

5. The method according to claim 1 wherein the 2H-benzimidazol-2-one, 1,3-dihydro-1-(2-{4[3-(trifluoromethyl) pheny[-1-][piperazinyl}ethyl) (flibanserin) is employed in a dosage amount of 1 mg to 20 mg.

* * * * *